United States Patent [19]

Mayer et al.

[11] Patent Number: 4,719,112

[45] Date of Patent: * Jan. 12, 1988

[54] FOAM CAPSULES

[75] Inventors: Jean P. Mayer, Colmar, France; Fritz Wittwer, Lupsingen, Switzerland

[73] Assignee: Warner-Lambert Company, Morris Plains, N.J.

[*] Notice: The portion of the term of this patent subsequent to Sep. 2, 2003 has been disclaimed.

[21] Appl. No.: 766,475

[22] Filed: Aug. 19, 1985

Related U.S. Application Data

[60] Continuation-in-part of Ser. No. 589,836, Mar. 15, 1984, abandoned, which is a continuation-in-part of Ser. No. 484,723, Apr. 13, 1983, Pat. No. 4,500,358, which is a division of Ser. No. 438,147, Oct. 29, 1982, abandoned.

[51] Int. Cl.⁴ .................. A61K 9/48; A61K 3/07; C08J 9/30; C08L 89/04
[52] U.S. Cl. .................. 424/456; 424/DIG. 7; 424/453; 514/962; 514/963
[58] Field of Search .................. 424/DIG. 7, 37, 453, 424/456; 514/962, 963

[56] References Cited

U.S. PATENT DOCUMENTS

| | | | |
|---|---|---|---|
| 3,173,840 | 3/1965 | Hostetler et al. | 424/21 |
| 3,555,132 | 1/1971 | Benning | 521/186 |
| 3,620,759 | 11/1971 | Maddox | 424/15 |
| 3,823,816 | 7/1974 | Controulis et al. | 424/15 |
| 4,086,331 | 4/1978 | Neumann | 424/45 |
| 4,331,547 | 5/1982 | Stotts et al. | 106/125 |
| 4,500,358 | 2/1985 | Mayer et al. | 106/122 |
| 4,609,403 | 9/1986 | Wittwer et al. | 106/122 |

Primary Examiner—Ronald W. Griffin
Attorney, Agent, or Firm—Howard Olevsky; Stephen Raines

[57] ABSTRACT

Foam capsules with telescopically engaged body and cap portions, also known as hard shell capsules, having a special wall structure, obtained by a microdispersion of a gas in a gelatin solution.

The capsule body and cap portions are formed by dip-molding the film-forming mixture obtained by a microdispersion of the gas in a gelatin solution; optionally with the inclusion of a plasticizer and/or coloring agent, and/or flavoring agent, and/or foam stabilizer, and/or gelatin extender.

By a suitable choice of the gas proportion in the capsule wall and its micronization level, it is possible, within certain limits, to control the capsule wall disintegration speed and its opacity. In addition, inclusion of gas bubbles into the capsule wall lowers the gelatin content for a foam capsule and provides energy saving during the process due to a faster drying of the wall, thereby providing lower cost prices for the production of pharmaceutically acceptable capsules.

4 Claims, No Drawings

FOAM CAPSULES

CROSS REFERENCE TO RELATED APPLICATIONS

This application is a continuation-in-part of Ser. No. 589,836 filed Mar. 15, 1984 now abandoned, which is a continuation-in-part of Ser. No. 484,723 filed Apr. 13, 1983 now U.S. Pat. No. 4,500,358 issued Feb. 19, 1985 which is a division of Ser. No. 438,147 filed Oct. 29, 1982 now abandoned.

SUMMARY

The present invention relates to a foam capsule. More particularly, the invention relates to pharmaceutically acceptable capsules having capsule body and cap portions, formed by dipmolding, using a film-forming mixture obtained by a microdispersion of a suitable gas in a gelatin solution;

In this application, when the term "gelatin" is used, it is also understood to include other proteins similar to gelatin in physical and chemical properties, and gelatin combined with starch or derivatives thereof.

As used herein, the term "gelatin" means gelatin and derivatives thereof.

As used herein, the term "gelatin foam" means a homogeneous mixture obtained by microdispersion of a gas in a gelatin solution.

The term "capsules" means hard shell capsules having telescopically engaged body and cap portions obtained by a dipmolding technique (see U.S. Pat. No. 3,173,840.)

The term "foam capsules" means such capsules, obtained by dipmolding into gelatin foams, the wall of which being formed by a homogeneous microdispersion of gas in dry gelatin.

As is known, capsules are a preferred form of administration for medicaments and similar products. However, in many cases, the disintegration speed of the gelatin capsules can vary considerably depending on the composition of the contents. For example, the disintegration of capsules containing a lipophilic medicament is delayed because of the lipophilic properties of the content. The rapid release of the medicament is thereby impaired which can have a detrimental effect on its bioavailability. In order to avoid these disadvantages, attempts have been made to ensure a rapid release of the capsule contents by means of a suitable form of the capsule walls, for example by providing them with holes or other apertures, as described in U.S. Pat. No. 3,620,759. Such capsules have, however, the disadvantage that, in the case of pulverulent contents, premature release of the contents takes place, during storage or transport. In order to avoid this undesirable, premature release of the capsules' contents, capsules of this type, having holes or other apertures, have been provided completely or partially with a coating of a water-soluble material, as described in U.S. Pat. No. 3,823,816. Although the undesirable, premature release of the capsules' contents can be largely avoided in this manner, the production of such capsule is difficult and expensive.

The objective of this invention was therefore to modify the capsule wall of gelatin capsules provided for medicinal and other purposes in such a manner that a control, particularly an acceleration, of the capsule disintegration can be achieved in a simple manner.

On the other hand, many additives used in pharmaceutical materials are now being critically examined. For example, titanium dioxide, commonly used as an opacifier in hard shell gelatin capsules, is under examination as to whether or not it is pharmaceutically acceptable.

A new capsule type, the wall of which would be opaque without addition of titanium dioxide or other similar chemicals and which could therefore contain only natural and biodegradable products, would have important advantages over conventional hard shell gelatin capsules.

It has been found in the present invention that it is possible to obtain white opaque film-forming mixtures by simple inclusion, followed by micronization, of suitable gases such as air, oxygen, nitrogen, carbon dioxide, argon, etc. into natural transparent gelatin solutions. The opacity and white color shade of the foam capsules obtained by dipmolding into such film-forming mixtures, is a function of the included gas quantity and of its micronization level.

It has also been found in the present invention that the stability of the foam increased in the following order or microdispersion of gases: carbon dioxide, oxygen, air, nitrogen and argon. However, economic considerations favor the use of air and nitrogen.

It has also been found that the particular structure of the wall of such foam capsules, assures, with regard to conventional hard shell gelatin capsules with a same wall thickness, a notable increase of the disintegration speed. This disintegration time can be varied by modifying both gas content and thickness of the wall. Increasing the gas content and/or decreasing the wall thickness, the disintegration time is reduced. Decreasing the gas content and/or increasing the wall thickness, the disintegration time is increased.

As a result of these discoveries, it was possible to achieve the objectives of the present invention and to provide a hard shell gelatin capsule, the wall of which is opaque without additives such as titanium dioxide, that decomposes at a particularly higher speed which can be controlled and which is suitable for medicinal purposes. This foam capsule is characterized in that the material forming the capsule wall is a foam obtained by microdispersion of a suitable gas in gelatin, optionally with the inclusion of a plasticizer and/or a coloring agent, and/or a flavoring agent, and/or a foam stabilizer, and/or a gelatin extender.

DESCRIPTION OF THE PRIOR ART

Prior art for gelatin based foams is contained in the following patents:

1. U.S. Pat. No. 3,555,132, issued Jan. 12, 1971 to C. J. Benning, which discloses a process for producing an aldehyde-hardened gelatin foam consisting of the steps of:
    (a) adding 4 to 24 parts of said aldehyde to a solution of 50% by weight of gelatin in water to insolubilize the gelatin;
    (b) beating the wetted solution into a foam;
    (c) shaping the foam by placing it in a mold;
    (d) removing the shaped foam from the mold; and
    (e) simultaneously heating and drying the foam at temperatures between about 51° C. to 93° C. The resulting stiff and rigid foam blocks have densities of 0.065 to 0.080 g/cm$^3$ and are intended for shock-absorbing and insulating purposes.

2. U.S. Pat. No. 4,086,331, issued Apr. 25, 1978 to P. Neumann, which discloses a composition and a method for the generation of gelatin-based stabilized foams for use in medicine for the treating of runs and in agriculture for the coating of plants.

Said compositions comprise an aqueous solution of 0.1% to 3% by weight of gelatin, 0.01 to 0.2% by weight of an anionic surface active agent; an amount sufficient to stabilize said gelatin based foam up to 1% by weight of a water soluble ferrous salt; and an amount sufficient of glutaraldehyde to maintain said composition in liquid state.

Said foaming method consists of passing a stream of air or gas through orifices or sintered metal or of aerosol generation at temperatures of between 5° to about 30° C. The resulting foams have densities in the wet state between 0.0035 to 0.20 g/cm$^3$ and bubble diameter are in broad range of between about 1 mm to 10 mm.

3. U.S. Pat. No. 4,331,547, issued May 25, 1982 to E. J. Stotts and G. S. Arbuthnot discloses a thermal insulating foam made from a collagen protein such as animal glue; and a method of production thereof. The dry density of the foam is of the order of 0.004 to 0.008 g/cm$^3$.

DESCRIPTION OF THE INVENTION

The gelatin foams, suitable to obtain foam capsules according to the present invention, are made from aqueous solutions of gelatin comprising between 10 to 50% by weight of gelatin, better in the range of 15 to 35% and best in the range 21 to 28%. Different grades of pure gelatins or mixtures thereof can be used at pH values between 3.0 to 10.0, with better results in the range of pH 4.0 to 7.0.

The foam may be produced according to any of a number of common methods, wherein air, or a gas such as nitrogen, oxygen, argon, carbon dioxide or another suitable gas, or a mixture thereof, is mixed with the aqueous gelatin solution and microdispersed therein.

This microdispersion is generally obtained by direct application of mechanical energy, in an operation where the aqueous gelatin solution is brought and kept in violent motion in the presence of the gas. This may be done batchwise or continuously, in open or closed reservoirs.

Foaming equipment including high-speed blenders and whipping or beating equipments, especially those commonly used in the food industry as for example a "baker's whip" in which a wire whisk is both rotated and travels in a circular path, may be successfully adapted for the generation of gelatin foams in accordance with the present invention, provided that the characteristics of said equipments are or may be adapted to obtain a sufficient microdispersion level of the gas bubbles within the foam to avoid any hole in the capsule wall and to ensure an acceptable opacity of said wall.

Insofar as the microdispersed gas bubbles in accordance with the present invention must have very small diameters distributed within a narrow range to lead to optimal foam capsules qualities microdispersing equipment based on the application of high shear stresses to said gas bubbles are preferred as foaming equipment. Such equipment principally comprise a rotor, rotating at high speed within a stator so as to force the gas and aqueous gelatin mixture through calibrated holes or gaps defined by the respective configurations of rotor and stator. Such equipments include centrifugal emulsifying devices and continuous pressure beaters.

In light of industrial scale production concerns, continuous pressure beaters are preferred.

Centrifugal emulsifying devices are immersed into aqueous gelatin solutions contained in open or closed tanks fitted with one or more gas inlets to introduce said gas into said gelatin solutions. The rotation at high speed of the rotor, closely fitted to a perforated stator, causes the circulation of the gelatin solution and gas mixture within the tank and through the centrifugal emulsifying device where the gas bubbles are forced by the rotor through the gap between the rotor and stator and through the perforations of the stator, to be microdispersed. The diameter of the microdispersed gas bubbles is in a considerable measure controlled by the rotation speed of the rotor and the dimensions of the perforations of the stator and the gap between rotor and stator. Such centrifugal emulsifying devices may be used for batch-production of gelatin foam, in which case a controlled quantity of gas is first mixed with a gelatin solution contained in a tank and microdispersed to get a gelatin foam batch with defined characteristics, and then said gelatin foam batch is used to dip-mold foam capsules. Until complete consumption of the batch, the centrifugal emulsifying device must continuously microdisperse the gas bubbles to maintain a constant foam quality, otherwise the gas bubbles grow and collapse, causing air losses, while the aqueous gelatin solution tends to drain, causing demixion. In another embodiment of the present invention such batch-production of gelatin foam may be transformed into continuous production provided that the foam quantity and quality, within the tank where the centrifugal emulsifying device operates, is continuously monitored and regulated by adequate addition of fresh aqueous gelatin solution and/or water and/or gas.

The gas/gelatin solution ratio in the foam is controlled by the corresponding injection rates. The microdispersion level of the gas bubbles is, in a considerable measure, controlled by the number of teeth, the chamber configuration, the contact time of the foam in the mixing head, and the revolving speed of the rotor in the stator.

For capsule production, suitable metal mold pins are dipped according to specific dipping profiles into the gelatin foam and the wet film thus formed on the pins upon lifting from the foam is dried gradually to obtain the desired foam capsule parts. The wall thickness of capsules produced by dip molding depends on the viscosity of the gelatin foam. If a thin-walled capsule is desired, more water and/or less gas are used in order to lower the viscosity, whereas if a thick-walled capsule is desired, less water and/or more gas are added in order to increase the viscosity.

The wall thickness of the capsule is also dependent on the temperature of the gelatin foam. Depending upon the desired wall thickness and on the foam composition, the foam in the dipping dish is kept at a temperature between 30° to 65° C., better between 40° and 50° C.

Suitable gelatin foams for obtaining foam capsules by dip-molding according to the present invention are characterized by a gas content between about 8 to 70% vol/vol of the gelatin foam, better between 9 to 45%, and best between 13 to 31%; a density between about 0.3 to 1.1 g/cm 3, better between 0.6 to 0.95 g/cm 3 and best between 0.75 to 0.90 g/cm$^3$; a viscosity, when measured at 50° C., between about 200 and 2,000 centipoises, better between 400 to 1000 centipoises and best between 500 to 900 centipoises; and, for obtaining a desired opacity and optimal properties of the foam capsules by a diameter of the microdispersed gas bubbles from above 0 to about 150 microns, preferably between about 0.1 to 70 microns, the most preferred being between 1 to 50 microns.

In the manufacturing of conventional gelatin capsules with telescopically joined body and cap parts, dip-molding is performed in a dish containing the film-forming gelatin solution most of said gelatin solution being continuously circulated within the dish over several hours since only a very small quantity thereof is withdrawn each time when mold-pins are dipped.

Considering the above mentioned relative instability of gelatin foams as a function of time (growing and collapsing of gas bubbles, draining of the gelatin solution), one preferably includes the foaming equipment, better a tank fitted with a centrifugal emulsifying device or a continuous pressure beater, in a loop of an apparatus wherein the gelatin foam flows continuously from the foaming equipment to a dish where dip-molding is performed and, instead of remaining there over hours, is continuously recirculated through the foaming equipment wherein the gas bubbles are submitted again to a new microdispersion and where regulation of the optimal gas/water/gelatin ratios in the foam takes place before said gelatin foam, for which a constant quality may thus be maintained over long time periods, flows again to the dish for dip-molding and the same cycle is repeated again.

In addition, since microdispersing generates considerable heat, above mentioned foaming equipment are preferably equipped with a heat exchanger to keep the gelatin foam below a given temperature to avoid gelatin degradation and above the gelling temperature of said gelatin foam.

A constant foam quality regulation is assured by simultaneous in-line viscosity and density measurements and subsequent addition of water and/or air and/or fresh gelatin solution.

In some cases, particularly when more diluted gelatin solutions are used, foam stabilizing agents may be added at varying concentrations. In general amounts of about 0.01 to 5% and preferably at 0.05 to 0.5% based upon the weight of gelatin have been found effective. Suitable illustrative foam stabilizing agents include:

viscosity increasing agents selected from a group consisting of alginic acid and salts thereof, xanthancellulose derivatives including carboxymethylcellulose, hydroxypropylcellulose, and microcrystalline cellulose;

vegetable gums consisting of carrageenates, pectin, and agar;

proteins consisting of egg white and its derivatives, including pan-dried or spray-dried egg albumin; and hydrolyzed animal proteins;

esters consisting of sucrose esters, fatty acid esters and ethoxylates thereof, including polyglycerol and sorbitol derivatives thereof; glycerides and derivatives thereof including succinyl monoglycerides; acetic-, lactic-, citric-, or acetylated tartaric acid esters of monoglycerides, glycosides, lanolin and its derivatives, and mixtures thereof;

non-ionic surfactants consisting of fatty acid alkylolamides or ethoxylates thereof; amines and amine oxides with at least one long chain substituent of between 8 to 18 carbon atoms, and particularly N,N-dimethyl-dodecylamine; linear or branched long chain alcohols with between 8 to 18 carbon atoms, and particularly lauryl alcohol; and mixtures thereof;

anionic surfactants selected from alkylarylsulphonates, the alphatic chain, linear or branched, bearing 8 to 14 carbon atoms, the aromatic nucleus being benzene or toluene, the cation being sodium, ammonium or triethanolamonium, particularly sodium dodecylbenzenesulphonate; and fatty alcohol sulfates with a linear or branched aliphatic chain bearing 8 to 18 carbon atoms, the cation being selected from the group of sodium, ammonium, mono-, di- and triethylammonium, particularly sodium lauryl sulphate; ethersulphates including polyethoxylated derivatives of the above alcohol sulfates, the number of ethoxy rests being between 1 and 4; and mixtures thereof;

metal salts including aluminum, calcium, potassium, and iron salts; and pharmaceutically acceptable combinations of the above, particularly mixtures of egg albumin and microcrystalline cellulose or mixtures of non-ionic and anionic surfactants, particularly sodium lauryl sulphate and sorbitol monooleate or sodium lauryl sulphate and coconut fatty acid diethanolamide;

anionic surfactants such as alkylarylsulphonates, particularly sodium dodecylbenzenesulfonic acid, and alcoholsulphates, particularly sodium lauryl sulphate, ethersulphates and the like;

metal salts such as aluminum, calcium, potassium, and iron salts, and the like; and combinations of the above, particularly mixtures of egg albumin and microcrystalline cellulose or mixtures of non-ionic and anionic surfactants such as, for example, sodium lauryl sulphate and sorbitol monooleate or sodium lauryl sulphate and coconut fatty acid diethanolamide.

It must be noted, of course, that among the above-mentioned stabilizers, only approved foam stabilizers may be used for the production of foam capsules for food or pharmaceutical uses.

For manufacturing hard shell foam capsules according to the present invention, the utilization of pharmaceutical goods coloring agents, flavoring agents and plasticizers leads to optimal product qualities without destroying or substantially altering their valuable physical properties.

Food or pharmaceutically acceptable coloring agents are optionally used, including synthetic dyes, particularly azo-dyes, and certified lakes, as iron oxides and hydroxides, titanium dioxide, and natural dyes used alone or in combination in varying amounts; in concentrations of between about 0.001 to 10%, better between 0.001 to 5% based upon the weight of dry gelatin.

Flavoring agents accepted for pharmaceutical and food use are usually prepared by or derived from synthetic flavor oils and/or oils derived from plants, leaves, flowers, fruits, etc. as well as combinations thereof. Representative flavor oils include peppermint oil, cinnamon oil, spearmint oil, etc. Furthermore, natural or synthetic fruit flavors such as oils including lime, grape, orange, lemon, grapefruit and fruit essence including apple, pineapple, cherry, strawberry, etc. can be used as well as natural and synthetic vanillin, or ethyl vanillin.

The above flavoring agents are generally used at a concentration of about 0.01% to about 6% by weight on dry gelatin or derivatives thereof; better at about 0.2 to about 2%.

The plasticizers may be selected from the following groups:

a. Poly-hydroxy alcohols including glycerol, sorbitol and mannitol;
b. Dialkylphtalates preferably where alkyl is butyl;
c. Lower alkyl citrates wherein lower alkyl has 1 to 6 carbon atoms;
d. Glycols and polyglycols including polyethyleneglycol with a molecular weight range of about 200 to 40,000 dalton, methoxy-propylene-glycol, and 1,2-propyleneglycol;
e. Esters of polyhydroxy-alcohols including mono-, di- and tri-acetate of glycerol;
f. Ricinoleic acid and esters thereof; and
g. Related materials and mixtures of the above.

The plastics may be used at various concentrations of between about 0.2 to 10% better between 0.2 to 5% based upon the weight of dry gelatin.

In addition it has been found that the foam soft gelatin capsules of the present invention can be produced with various grades of gelatin combined with extenders of between about 2 to 40% content, by weight, better between about 5 to 20%, selected from the group of sunflower proteins, soybean proteins, cotton seed proteins, peanut proteins, rape seed proteins, and better defatted qualities thereof, as well as native starches, especially potato and corn starches, or derivatives thereof, including pregelatinized starches, thin-boiling starches, dextrins, and hydroxyalkystarches. For manufacturing capsules with such gelatin extenders, and combinations thereof, the same kind of coloring agents, plasticizers, foam stabilizers and flavoring agents as described above, are suitable.

The foam capsules according to the present invention can be made, if desired with one or more locking features.

In the same manner as conventional hard shell gelatin capsules, foam capsules show optimal properties when the wall moisture content is between about 12 to 16%. In spite of the gas inclusion, the wall elasticity of foam capsules is similar to that of conventional hard shell gelatin capsules. An important advantage of the foam capsule is that it is considerably cheaper in manufacture than conventional hard shell gelatin capsules since a smaller amount of gelatin is required. For example, gelatin savings of between 40 to 50% can be reached without substantially altering the mechanical properties of foam capsules. In addition, since the particular structure of the wall of foam capsules provides a considerably increased exchange surface, an appreciable energy saving can be obtained during the manufacturing process because the wet half shells dry more easily and more rapidly on the mold bars than conventional hard gelatin capsule shells.

As mentioned above, the foam capsules have opaque walls, which effect is exclusively due to the homogeneous gas dispersion in the wall material and thus avoids the use of opacifying agents such as titanium dioxide or the like.

As described above, the possibility to obtain with foam capsules, within certain limits, controlled disintegration times and particularly shorter disintegration times than with conventional hard shell capsules, makes them suitable for a wide range of uses.

For example, capsules with moderate gas ratios in the wall, as obtained by dipping into gelatin foams having gas contents of between approximately 8 to 28% vol/vol, are useful for classical oral administration of medicaments. This means that they can be ingested without particular risk of premature opening in the mouth or in the esophagus. Their advantages over conventional hard shell gelatin capsules are a faster disintegration in the stomach, thereby maintaining an improved bioavailability of their contents, and less local irritations of the gastric mucous membrane may be obtained.

On the other hand, foam capsules with higher gas ratios in the wall are not adapted for classical oral administrations since the disintegration is so fast that a premature content release occurs in the mouth or in the esophagus. This particularity makes them especially suitable as chewing-capsules, or as capsules for sublingual administration, or in all cases where a fast absorption of the medicament by the mucous membrane of the mouth is desirable, as for nitroglycerine and certain steroid hormones, and particularly for those which are unstable under acidic conditions and are destroyed in the stomach.

In some cases, at low gas ratios in the wall and with thicker walls, the disintegration time of foam capsules is comparable with that of conventional hard shell gelatin capsules. A longer disintegration time is also obtainable with foam capsules. In this particular case the main advantage of foam capsules is the opacity of the wall without addition of opacifying agents.

An interesting effect of the micronization of gas bubbles in the wall of foam capsules is to provide a special configuration to the outer surface of the capsule wall (juxtaposed microbubbles) which confers to the foam capsules, when using only current approved natural and synthetic dyestuffs for pharmaceuticals, special and more brilliant color shades, like opalescent or pearly, which cannot be obtained for conventional hard shell gelatin capsules with the same dyestuffs.

Foam capsules may also be useful in other fields than pharmaceutical purposes, particularly in those cases where single dosage forms with a fast disintegration would be ideal such as:

food packaging, as for powdered instant coffee or spices;
candy manufacturing;
fertilization of ornamental plants and/or indoor plants;
packing of sensitive seeds in combination with protective agents and/or fertilizers; and packing of single dyestuffs (or mixtures of various dyes) doses, at precise weight for quick preparation of dyestuff solutions and the like. The present invention is illustrated by following examples:

EXAMPLE 1

A natural transparent aqueous solution of gelatin, at a concentration of 24% weight/weight, with an initial viscosity of 300 centipoise is poured into a foaming reservoir fitted with a water jacket, a centrifugal emulsifying device and an air introduction pipe.

During a first foaming step, air is introduced into the solution and micronized by the emulsifier, rotating at full speed (2,800 rpm), until an air content of 23% volume/volume, and a satisfactory micronization of the air bubbles are reached. The white opaque foam obtained has a temperature of 48° C. (water jacket at 45° C.), a viscosity of 800 centipoise and a density of 0.8 g/cm$^3$.

In a second step, an exit valve or faucet from the foaming reservoir is opened and the foam flows by gravity towards the dipping dish wherein it is distributed through a longitudinal slit. The foam overflow is collected and reintroduced with a peristaltic pump into the foaming reservoir where it is recirculated through the emulsifier. The foam quality regulation is assured, over several hours, by simultaneous in-line viscosity and density measurements and subsequent addition of water and/or air and/or fresh gelatin solution.

For the formation of capsule halves by the dip-molding technique, previously lubricated metallic cap and body mold pins are dipped into the gelatin foam which flows through the dipping dish and are withdrawn and lifted slowly in conventional fashion to provide even distribution of the foam film layer over the effective area of each mold pin. The coated pins are then kept stationary for a sufficient period to gellify the film layer on the pin. The capsule halves thus formed are dried by blowing with air at about 30% relative humidity and at about 30° C., and are removed from the pins, trimmed and joined together with the other halves of the capsule to provide the finished foam capsule ready for filling.

To confirm that the obtained white opaque, slightly opalescent, foam capsules obtained have the described properties, the capsules are filled with lactose and subjected to a standard disintegration test in an Erweka apparatus according to the method described in the European Phamacopeia, 2nd. Edition, 1980, Part 1, V.5.1.1.

TABLE 1

Compared Disintegration Times in Seconds Between Foam Capsules and Conventional Gelatin Capsules

| Capsule type | Wall thickness ($10^{-3}$ in) | Mean opening time (on 6 capsules) | Mean disintegration time (on 6 capsules) |
|---|---|---|---|
| Foam | 5 | 30 | 81 |
| Conventional capsule | 4 | 82 | 195 |

As Table 1 shows, in spite of a 25% thicker wall, the disintegration of the tested foam capsules is 58% faster than for conventional capsules.

TABLE 2

Weight Evaluation

| | |
|---|---|
| Mean weight foam capsules | 52 mg |
| Normal reference capsule | 78 mg |

As shown in Table 2, manufacturing of the described foam capsules allows a gelatin saving of 33%.

TABLE 3

Compared drying speeds at 30° C. and 30% RH (measured is the required time for to obtain capsule walls with 20% moisture content)

| Capsule type | Time (min.) |
|---|---|
| Foam Capsule | 24 |
| Normal ref. capsule | 38 |

Table 3 shows that the drying of the described foam capsules is 37% faster than for conventional capsules.

EXAMPLE 2

The production of the foam capsules was the same as in Example 1, but the influence of different air content values and wall thicknesses on disintegration time was checked.

TABLE 4

Disintegration time as a function of air content and wall thickness (on every 6 capsules)

| Sample reference capsule | % of air in the foam before drying | Wall thickness ($.10^{-3}$ inches) | Disintegration time (in sec.) |
|---|---|---|---|
| conventional standard | — | 4 | 195 |
| Foam 1 | 15% | 4 | 149 |
| Foam 2 | 15% | 5.5 | 173 |
| Foam 3 | 20% | 5.5 | 140 |
| Foam 4 | 23% | 5 | 81 |
| Foam 5 | 23% | 6 | 108 |
| Foam 6 | 26% | 6.5 | 96 |
| Foam 7 | 29% | 5.5 | 64 |

The above demonstrates that with a suitable choice of the air proportion in the capsule wall and of the wall thickness, it is possible, within certain limits to control the disintegration time.

EXAMPLE 3

The production of colored foam capsules was the same as in Example 1, but, before foam generation, the following dyes or pigments were mixed with the gelatin solution at a concentration of 0.5% based upon weight of dry gelatin.
Red: azorubine
Blue: patent blue
Yellow: tartrazine
Black: black iron oxide The colored foam capsules were opaque, and had similar disintegration times, as the corresponding white opaque capsules described in Example 1 above. In addition, the colored foam capsules were characterized by new, more brilliant, opalescentlike, color shades than for conventional capsules.

EXAMPLE 4

The production of flavored capsules was the same as in Example 1 but, before foam generation, peppermint oil as a flavoring agent was added at a concentration of 0.6% based upon the weight of dry gelatin.

EXAMPLE 5

Example 1 was repeated by adding 2% of glycerol, based on dry gelatin weight, in the gelatin solution. The additive did not affect the ability to generate a suitable foam, and the disintegration time of the obtained capsules remained similar.

EXAMPLE 6

Example 1 was repeated by adding 0.2% sodium lauryl sulphate and 0.2% sorbitan monooleate, based on dry gelatin weight, in the gelatin solution. The additives did not affect the disintegration time of the obtained capsules, but increased notably the lifetime of the gelatin foam circulating in the dish.

EXAMPLE 7

Example 1 was repeated by replacing the air with nitrogen. This replacement did not affect the ability to generate a suitable foam, and the disintegration time of the obtained capsules remained similar.

While there have been described and illustrated several embodiments of the present invention, the scope and working range of the invention shall not be limited by the examples given above. The invention comprises as well various changes and modifications which will occur to those skilled in the art.

It is intended in the appended claims to cover all such changes and modifications as fall within the true spirit and scope of the present invention.

What is claimed is:

1. A physiologically acceptable hard gelatin foam capsule adapted to be filled with a medicament, which comprises a body and a cap, said body and said cap being constructed of a material having a pore size of about 0.1 to 70 microns and a density of about 0.6 to 0.95 g/cc.

2. The foam capsule of claim 1 wherein the pore size is 1 to 50 microns.

3. The foam capsule of claim 1 wherein the foam capsule comprises gelatin and said body and said cap have a wall thickness of 0.004 to 0.0065 inc.

4. The foam capsule of claim 3 wherein the foam capsule comprises gelatin and said body and said cap have a wall thickness of 0.004 to 0.0065 inc.

* * * * *